United States Patent
Matsumoto (10) Patent No.: US 11,812,920 B2
(45) Date of Patent: Nov. 14, 2023

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 156 days.

(21) Appl. No.: 16/923,966

(22) Filed: Jul. 8, 2020

(65) Prior Publication Data
US 2020/0330077 A1   Oct. 22, 2020

Related U.S. Application Data (63) Continuation of application No. PCT/JP2018/042697, filed on Nov. 19, 2018.

(30) Foreign Application Priority Data

Feb. 23, 2018 (JP) .................................. 2018-030808

(51) Int. Cl.
*A61B 8/00*  (2006.01)
*A61B 8/08*  (2006.01)

(52) U.S. Cl.
CPC ............ *A61B 8/543* (2013.01); *A61B 8/0883* (2013.01); *A61B 8/463* (2013.01)

(58) Field of Classification Search
None
See application file for complete search history.

(56) References Cited

U.S. PATENT DOCUMENTS 11,116,475 B2 *   9/2021   Ebata ................... A61B 8/5207
2010/0036248 A1   2/2010   Chouno
(Continued)

FOREIGN PATENT DOCUMENTS

CN   101522107 A   9/2009
CN   106551707 A   4/2017
(Continued)

OTHER PUBLICATIONS

International Search Report issued in PCT/JP2018/042697; dated Feb. 5, 2019.
(Continued)

*Primary Examiner* — Shahdeep Mohammed
(74) *Attorney, Agent, or Firm* — Studebaker & Brackett PC (57) ABSTRACT

An ultrasound diagnostic apparatus includes an image memory that stores ultrasound images of a plurality of frames a display unit that displays an ultrasound image of the selected frame selected by a user from the plurality of frames, a measurement unit that performs measurement for a measurement target part from the ultrasound image, a determination unit that determines whether the measurement has succeeded or failed, and a display switching unit that displays a measurement result in the selected frame on the display unit in a case in which measurement for the selected frame has succeeded and displays an ultrasound image of at least one peripheral frame different from the selected frame among the plurality of frames and a measurement result in the peripheral frame on the display unit in a case in which the measurement for the selected frame has failed.

15 Claims, 9 Drawing Sheets

(56) References Cited

U.S. PATENT DOCUMENTS

| | | | |
|---|---|---|---|
| 2011/0170755 A1 | 7/2011 | Buelow et al. | |
| 2012/0078101 A1 | 3/2012 | Kim et al. | |
| 2013/0331700 A1 | 12/2013 | Kawabata et al. | |
| 2016/0015365 A1* | 1/2016 | Li | A61B 8/085 600/438 |
| 2016/0019441 A1* | 1/2016 | Ryu | A61B 8/469 382/131 |
| 2016/0270757 A1 | 9/2016 | Toma et al. | |
| 2017/0090694 A1 | 3/2017 | Lee et al. | |
| 2018/0014810 A1 | 1/2018 | Chen et al. | |

FOREIGN PATENT DOCUMENTS

| | | |
|---|---|---|
| JP | 2010-269018 A | 12/2010 |
| JP | 2018-000339 A | 1/2018 |
| WO | 2008/044441 A1 | 4/2008 |
| WO | 2014/034148 A1 | 3/2014 |
| WO | 2017/211910 A1 | 12/2017 |

OTHER PUBLICATIONS

International Preliminary Report on Patentability and Written Opinion issued in PCT/JP2018/042697; dated Aug. 27, 2020.

Gabriella Csurka et al.; "Visual Categorization with Bags of Keypoints"; Proc. of ECCV Workshop on Statistical Learning in Computer Vision; 2004; pp. 59-74.

Alex Krizhevsky et al.; "ImageNet Classification with Deep Convolutional Neural Networks"; Advances in Neural Information Processing Systems 25; 2012; pp. 1106-1114.

The extended European search report issued by the European Patent Office dated Mar. 22, 2021, which corresponds to European Patent Application No. 18906750.7-1126 and is related to U.S. Appl. No. 16/923,966.

An Office Action mailed by China National Intellectual Property Administration dated Dec. 5, 2022, which corresponds to Chinese Patent Application No. 201880089979.0 and is related to U.S. Appl. No. 16/923,966; with English language translation.

* cited by examiner

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2018/042697 filed on Nov. 19, 2018, which claims priority under 35 U.S.C. § 119(a) to Japanese Patent Application No. 2018-030808 filed on Feb. 23, 2018. The above application is hereby expressly incorporated by reference, in its entirety, into the present application.

BACKGROUND OF THE INVENTION

1. Field of the Invention

The invention relates to an ultrasound diagnostic apparatus and a method for controlling an ultrasound diagnostic apparatus, and more particularly, to an ultrasound diagnostic apparatus and a method for controlling an ultrasound diagnostic apparatus that perform measurement for a part of a subject from an ultrasound image.

2. Description of the Related Art

An ultrasound diagnostic apparatus has been known as an apparatus that obtains an image of the inside of a subject. In general, the ultrasound diagnostic apparatus comprises an ultrasound probe having a transducer array in which a plurality of transducers are arranged. In a state where the ultrasound probe comes into contact with the body surface of the subject, an ultrasound beam is transmitted from the transducer array to the inside of the subject and the transducer array receives ultrasound echoes from the subject to obtain element data. Further, the ultrasound diagnostic apparatus electrically processes the obtained element data to generate an ultrasound image of the part of the subject.

In general, for example, the length and area of a part of the subject included in the generated ultrasound image are measured using the ultrasound image. For example, JP2010-269018A discloses an ultrasound diagnostic apparatus that performs measurement for a part of a subject using an ultrasound image. This ultrasound diagnostic apparatus disposes a marker for designating a measurement range at a set position on an ultrasound image set by a user and automatically performs measurement for a region designated by the marker.

SUMMARY OF THE INVENTION

In many cases, a measured value obtained by performing measurement for a part of a subject is used for diagnosis of the subject by, for example, a doctor. Therefore, it is desirable that the measured value related to a part of the subject is obtained by measurement based on a predetermined standard. For the measurement, a guideline in which standards, such as a measurement position and a measurement method, are defined is generally known.

The technique described in JP2010-269018A, it is not considered that measurement is performed for a part of the subject on the basis of a predetermined standard defined in the guideline. Therefore, in some cases, inappropriate values are obtained as the measured values used by, for example, a doctor to diagnose the subject.

In addition, a user, such as a doctor or a radiology technician, generally performs measurement for a part of the subject with a manual operation while viewing an ultrasound image. In particular, even in a case in which an unskilled user performs measurement while referring to the guideline, it may be difficult to perform measurement based on an appropriate standard and an appropriate measured value may not be obtained. In addition, in a case in which he user who does not know the existence of the guideline at all performs measurement for a part of the subject, measurement based on an appropriate standard is not performed, which makes it difficult to obtain an appropriate measured value.

The invention has been made in order to solve the above-mentioned problems of the related art and an object of the invention is to provide an ultrasound diagnostic apparatus and a method for controlling an ultrasound diagnostic apparatus that can perform measurement for a part of a subject on the basis of an appropriate standard, regardless of the skill level of a user.

In order to achieve the above object, according to the invention, there is provided an ultrasound diagnostic apparatus comprising: an image memory that stores ultrasound images of a plurality of frames which are continuous in time series and include a measurement target part of a subject as a measurement target; an operation unit that is used by a user to select one of the plurality of frames as a selected frame; a display unit that displays an ultrasound image of the selected frame; a measurement unit that performs measurement for the measurement target part of the subject from the ultrasound image; a determination unit that determines whether the measurement by the measurement unit has succeeded or failed; and a display switching unit that displays a measurement result in the selected frame on the display unit in a case in which the determination unit determines that measurement for the selected frame by the measurement unit has succeeded and displays an ultrasound image of at least one peripheral frame different from the selected frame among the plurality of frames stored in the image memory and a measurement result in the at least one peripheral frame on the display unit in a case in which the determination unit determines that the measurement for the selected frame by the measurement unit has failed.

In the peripheral frames, for a frame for which measurement has failed, the measurement result is not displayed.

The at least one peripheral frame may be a predetermined number of frames continuous with the selected frame.

Alternatively, the at least one peripheral frame may be all frames other than the selected frame among the frames within one heartbeat cycle including the selected frame. The measurement target part may be a part which moves periodically due to breathing of the subject or a part which moves periodically due to a heartbeat of the subject.

Alternatively, the at least one peripheral frame may be all frames other than the selected frame in a series of frames under measurement.

The at least one peripheral frame may be some frames from a frame subsequent to the selected frame to a frame, for which the determination unit determines that measurement has succeeded first, after the selected frame in time series or some frames from a frame, for which the determination unit determines that measurement has succeeded first, before the selected frame to a frame immediately before the selected frame in time series in a case in which the determination unit determines that the measurement for the selected frame has failed.

In a case in which the determination unit determines that the measurement for the selected frame has failed, the display switching unit may display a frame, for which the determination unit determines that measurement has succeeded, among the at least one peripheral frame so as to be highlighted.

Alternatively, the at least one peripheral frame may be a frame, for which the determination unit determines that measurement has succeeded, in a case in which the determination unit determines that the measurement for the selected frame has failed.

The display switching unit may notify the user of an error in a case in which the determination unit determines that the measurement for all of the selected frame and the at least one peripheral frame has failed.

For example, in a case in which the measurement target part is an inferior vena cava, the measurement unit may detect a boundary of a right atrium of the subject, specify a measurement position determined from the detected boundary of the right atrium, and measure a diameter of the inferior vena cava at the specified measurement position. The determination unit may determine that the measurement has failed in a case in which the measurement unit does not detect the boundary of the right atrium or in a case in which the measurement position is not specified.

The measurement result may include a measurement line for performing measurement for the measurement target part of the subject.

According to the invention, there is provided a method for controlling an ultrasound diagnostic apparatus. The method comprises: storing ultrasound images of a plurality of frames which are continuous in time series and include a measurement target part of a subject as a measurement target; displaying an ultrasound image of one selected frame selected by a user among the plurality of frames; performing measurement for the measurement target part of the subject from the selected frame; determining whether measurement for the selected frame has succeeded or failed; displaying a measurement result in the selected frame and the ultrasound image of the selected frame in a case in which it is determined that the measurement for the selected frame has succeeded; and displaying the ultrasound image of the selected frame, an ultrasound image of at least one peripheral frame different from the selected frame among the plurality of frames, and a measurement result in the at least one peripheral frame in a case in which it is determined that the measurement for the selected frame has failed.

According to the invention, the ultrasound diagnostic apparatus comprises the determination unit that determines whether measurement by the measurement unit has succeeded or failed and the display switching unit that displays the measurement result in the selected frame on the display unit in a case in which the determination unit determines that measurement for the selected frame by the measurement unit has succeeded and displays an ultrasound image of at least one peripheral frame different from the selected frame among the plurality of frames stored in the image memory and the measurement result in the at least one peripheral frame on the display unit in a case in which the determination unit determines that the measurement for the selected frame by the measurement unit has failed. Therefore, it is possible to perform measurement for a part of a subject on the basis of an appropriate standard, regardless of the skill level of the user.

DESCRIPTION OF THE PREFERRED EMBODIMENTS

Hereinafter, embodiments of the invention will be described with reference to the accompanying drawings.

Embodiment 1

Figure 1:
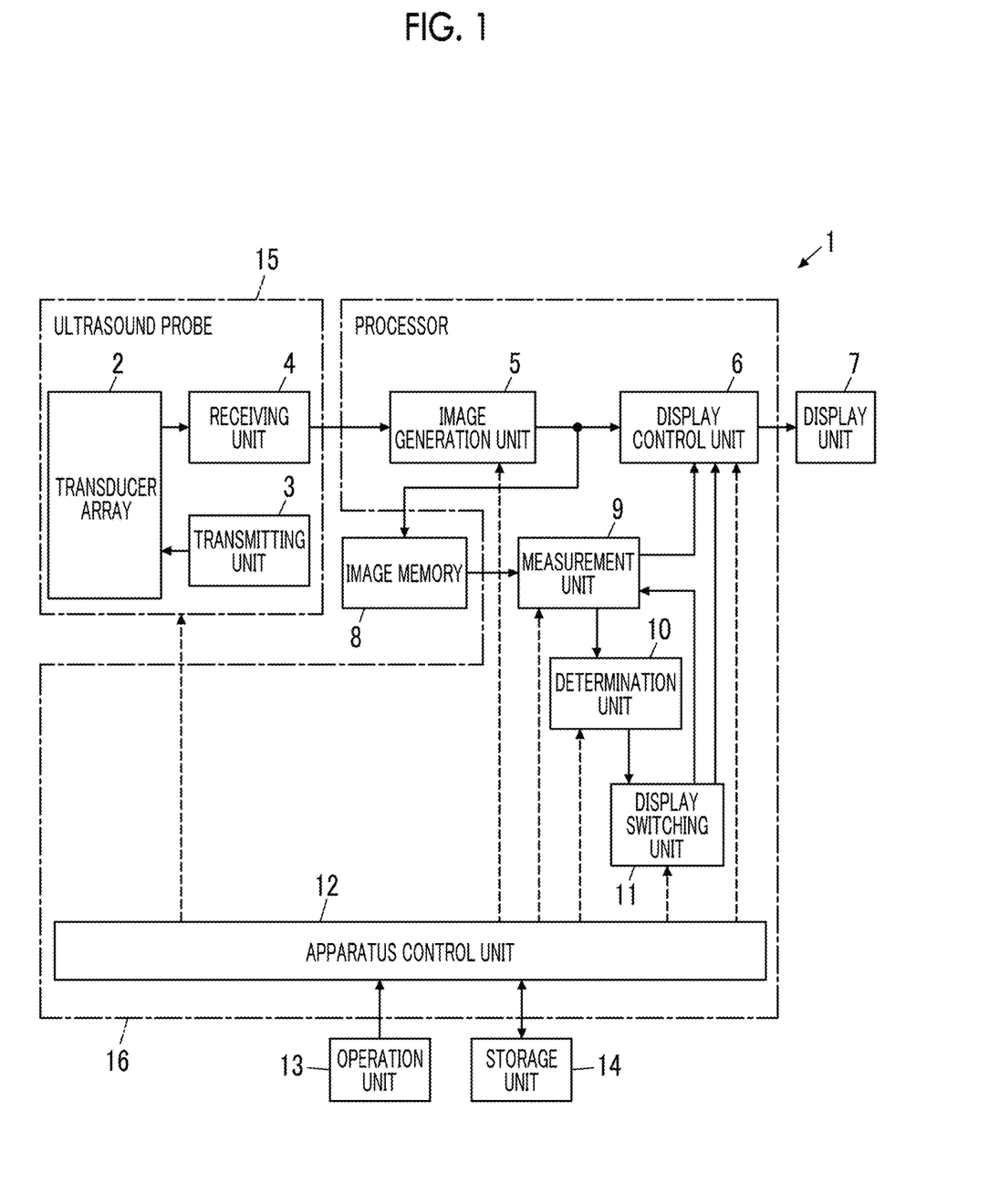
FIG. 1 is a block diagram illustrating a configuration of an ultrasound diagnostic apparatus according to Embodiment 1 of the invention.

FIG. 1 illustrates a configuration of an ultrasound diagnostic apparatus 1 according to Embodiment 1 of the invention. As illustrated in FIG. 1, the ultrasound diagnostic apparatus 1 comprises a transducer array 2. A transmitting unit 3 and a receiving unit 4 are connected to the transducer array 2. The transducer array 2, the transmitting unit 3, and the receiving unit 4 are included in an ultrasound probe 15. An image generation unit 5, a display control unit 6, and a display unit 7 are sequentially connected to the receiving unit 4. Further, an image memory 8 is connected to the image generation unit 5 and a measurement unit 9 is connected to the image memory 8. A determination unit 10 and a display switching unit 11 are sequentially connected to the measurement unit 9 and the display switching unit 11 is connected to the display control unit 6. The measurement unit 9 is connected to the display control unit 6.

Further, an apparatus control unit 12 is connected to the image generation unit 5, the display control unit 6, the measurement unit 9, the determination unit 10, the display switching unit 11, and the ultrasound probe 15. An operation unit 13 and a storage unit 14 are connected to the apparatus control unit 12. The apparatus control unit 12 and the storage unit 14 are connected such that they can exchange bidirectional information.

In addition, a processor 16 is configured by the image generation unit 5, the display control unit 6, the measurement unit 9, the determination unit 10, the display switching unit 11, and the apparatus control unit 12.

The transducer array 2 of the ultrasound probe 15 illustrated in FIG. 1 has a plurality of transducers that are one-dimensionally or two-dimensionally arranged. Each of the transducers transmits ultrasonic waves in response to a driving signal supplied from the transmitting unit 3. In addition, each of the transducers receives ultrasound echoes from a subject and outputs a received signal. For example, each transducer is configured by forming electrodes at both ends of a piezoelectric body consisting of piezoelectric ceramic typified by lead zirconate titanate (PZT), a polymer piezoelectric element typified by polyvinylidene difluoride (PVDF), or a piezoelectric single crystal typified by lead magnesium niobate-lead titanate (PMN-PT).

The transmitting unit 3 of the ultrasound probe 15 includes, for example, a plurality of pulse generators and supplies each driving signal to the plurality of transducers while adjusting the amount of delay such that the ultrasonic waves transmitted from the plurality of transducers of the transducer array 2 form an ultrasound beam, on the basis of a transmission delay pattern selected in response to a control signal from the apparatus control unit 12. As such, in a case in which a pulsed voltage or a continuous-wave voltage is applied to the electrodes of the plurality of transducers of the transducer array 2, the piezoelectric body is expanded and contracted and pulsed or continuous ultrasonic waves are generated from each transducer. An ultrasound beam is formed from a composite wave of the ultrasonic waves.

The transmitted ultrasound beam is reflected from a target, such as a part of the subject, and is propagated toward the transducer array 2 of the ultrasound probe 15. The ultrasound echoes propagated toward the transducer array 2 are received by each transducer forming the transducer array 2. In this case, each transducer forming the transducer array 2 is expanded and contracted by receiving the propagated ultrasound echoes, generates an electric signal, and outputs the electric signal to the receiving unit 4.

Figure 2:
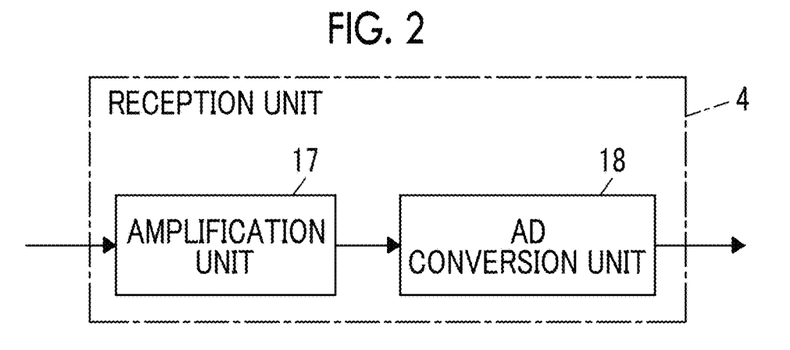
FIG. 2 is a block diagram illustrating an internal configuration of a receiving unit according to Embodiment 1 of the invention.

The receiving unit 4 of the ultrasound probe 15 processes the received signals output from the transducer array 2 in response to a control signal from the apparatus control unit 12. As illustrated in FIG. 2, the receiving unit 4 has a configuration in which an amplification unit 17 and an analog-digital (AD) conversion unit 18 are connected in series to each other. The amplification unit 17 amplifies the received signal input from each transducer forming the transducer array 2 and transmits the amplified received signal to the AD conversion unit 18. The AD conversion unit 18 converts the received signal transmitted from the amplification unit 17 into digital data and transmits the data to the image generation unit 5 of the processor 16.

Figure 3:
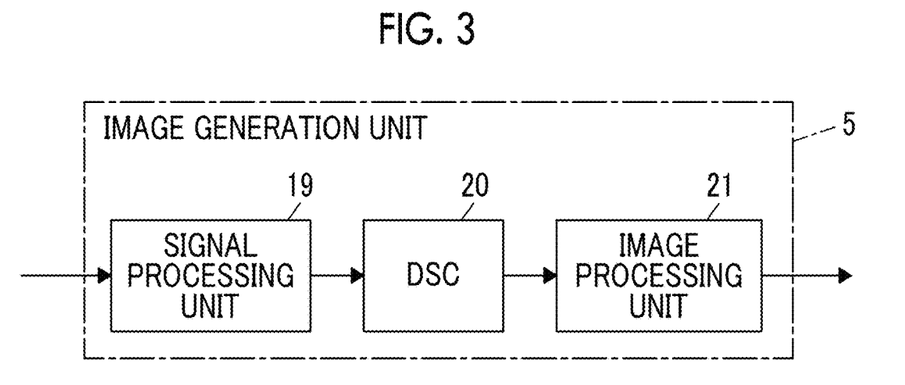
FIG. 3 is a block diagram illustrating an internal configuration of an image generation unit according to Embodiment 1 of the invention.

As illustrated in FIG. 3, the image generation unit 5 of the processor 16 has a configuration in which a signal processing unit 19, a digital scan converter (DSC) 20, and an image processing unit 21 are connected in series to each other. The signal processing unit 19 performs a reception focusing process that applies a delay to each data item of the received signals on the basis of a reception delay pattern selected according to a control signal from the apparatus control unit 12 and adds (phasing addition) the data items. A sound ray signal in which the focus of an ultrasound echo is narrowed to one scanning line is generated by the reception focusing process. In addition, the signal processing unit 19 corrects the attenuation of the generated sound ray signal due to a propagation distance according to the depth of the position where the ultrasonic waves are reflected, performs an envelope detection process to generate a B-mode image signal indicating the tissues in the subject. The generated B-mode image signal is output to the DSC 20.

The DSC 20 of the image generation unit 5 raster-converts the B-mode image signal into an image signal based on a general television signal scanning system to generate an ultrasound image. The image processing unit 21 of the image generation unit 5 performs various types of necessary image processing, brightness correction, gradation correction, sharpness correction, and color correction, for the image data obtained by the DSC 20 and outputs an ultrasound image to the display control unit 6 and the image memory 8.

The image memory 8 of the ultrasound diagnostic apparatus 1 stores a plurality of frames of ultrasound images that include a measurement target part of the subject to be measured and are continuous in time series. Here, for example, a recording medium, such as a hard disc drive (HDD), a solid state drive (SSD), a flexible disc (FD), and a magneto-optical disc (MO), a magnetic tape (MT), a random access memory (RAM), a compact disc (CD), a digital versatile disc (DVD), a secure digital card (SD card), or a universal serial bus memory (USB memory), or a server can be used as the image memory 8.

The measurement unit 9 of the processor 16 measures, for example, the length and area of the measurement target part of the subject from the ultrasound image stored in the image memory 8 on the basis of a predetermined standard. In this case, the measurement unit 9 analyzes the ultrasound image to recognize a part included in the ultrasound image, specifies a measurement position on the ultrasound image, and performs measurement at the specified measurement position. Here, the measurement position means, for example, a position where a measurement line for measuring the length is disposed and a position of a region for measuring the area.

Figure 4:
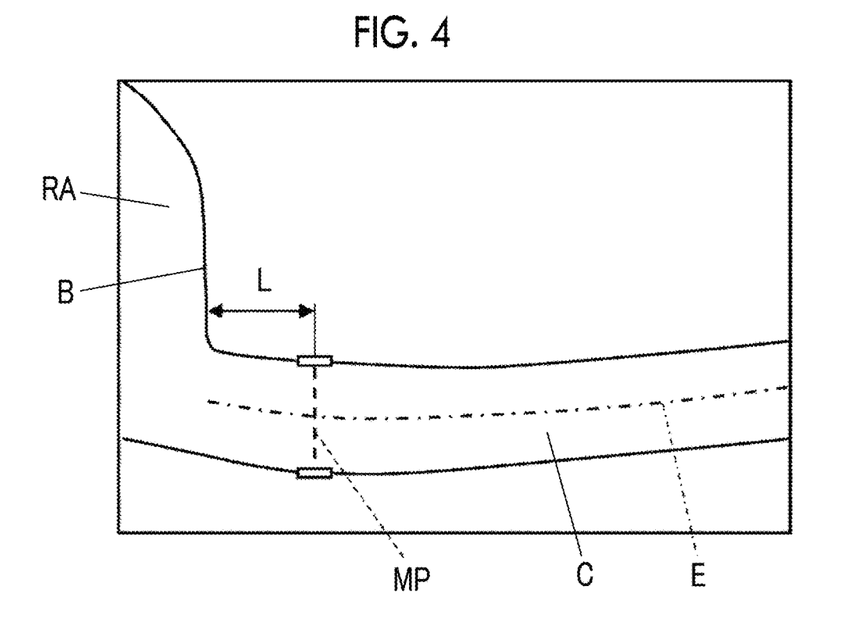
FIG. 4 is a diagram illustrating an example of a guideline for measuring the diameter of the inferior vena cava.

Here, in many cases, for example, a doctor uses the measured values, such as the length and the area measured from the ultrasound image, to diagnose the subject. It is desirable that the measured values are obtained by measurement based on a predetermined standard. Therefore, for the measurement, a guideline is generally known in which standards for, for example, a measurement position and a measurement method are defined for each measurement target part. For example, the following is defined: in a case in which the diameter of the inferior vena cava is measured, as illustrated in FIG. 4, a position that is 2 cm to 3 cm away from a boundary B of the right atrium RA along a central axis E of the inferior vena cava C is specified as a measurement position MP; a measurement line perpendicular to the central axis E of the inferior vena cava C is disposed at the measurement position MP; and measurement is performed. For example, the measurement unit 9 can set a measurement position for each measurement target part and perform measurement according to the guideline.

In a case in which an ultrasound image is analyzed, for example, the measurement unit 9 can perform so-called template matching that stores typical pattern data related to a part of the subject as a template in advance, calculates a similarity to the pattern data while searching the image with the template, and considers that a measurement target is present at the position where the similarity is equal to or greater than a threshold value and is maximum. In addition to simple template matching, for example, the following methods can be used to calculate the similarity: a machine learning method described in Csurka et al.: Visual Categorization with Bags of Keypoints, Proc. Of ECCV Workshop on Statistical Learning in Computer Vision, pp. 59-74 (2004); and a general image recognition method using deep learning described in Krizhevsk et al.: ImageNet Classification with Deep Convolutional Neural Networks, Advances in Neural Information Processing Systems 25, pp. 1106-1114 (2012).

The measurement unit 9 outputs, for example, a measured value, a measurement line, and a caliper as the obtained measurement results to the display control unit 6 and outputs, for example, information indicating whether or not the part required to specify a measurement position has been detected and information indicating whether or not a measurement position has been specified to the determination unit 10.

The determination unit 10 of the processor 16 determines whether the measurement by the measurement unit 9 has succeeded or failed on the basis of the measurement results including, for example, the information indicating whether or not the part required to specify a measurement position has been detected and the information indicating whether or not a measurement position has been specified which are output from the measurement unit 9. For example, the determination unit 10 may determine that the measurement by the measurement unit 9 has succeeded in a case in which a measured value has been obtained for the measurement target part and determines that the measurement by the measurement unit 9 has failed, for example, in a case in which the part required to specify the measurement position is not capable of being detected or in a case in which the measurement position is not capable of being specified. The determination unit 10 outputs the determination result to the display switching unit 11.

The display switching unit 11 of the processor 16 switches the display mode of the ultrasound image on the display unit 7 on the basis of the determination result from the determination unit 10, that is, whether the measurement by the measurement unit 9 has succeeded or failed. The switching of the display mode by the display switching unit 11 will be described in detail below.

The apparatus control unit 12 of the processor 16 controls each unit of the ultrasound diagnostic apparatus 1 on the basis of the program stored in advance in, for example, the storage unit 14 and the operation of the user through the operation unit 13.

The display control unit 6 of the processor 16 performs a predetermined process for the ultrasound image generated by the image generation unit 5 under the control of the apparatus control unit 12 and displays the ultrasound image on the display unit 7.

The display unit 7 of the ultrasound diagnostic apparatus 1 displays an image under the control of the display control unit 6 and includes a display device such as a liquid crystal display (LCD).

The operation unit 13 of the ultrasound diagnostic apparatus 1 is used by the user to perform an input operation and may comprise, for example, a keyboard, a mouse, a trackball, a touch pad, and a touch panel.

The storage unit 14 stores, for example, an operation program for the ultrasound diagnostic apparatus 1. Similarly to the image memory 8 of the ultrasound diagnostic apparatus 1, for example, a recording medium, such as an HDD, an SSD, an FD, an MO disc, an MT, a RAM, a CD, a DVD, an SD card, or a USB memory, or a server can be used as the storage unit 14.

The processor 16 including the image generation unit 5, the display control unit 6, the measurement unit 9, the determination unit 10, the display switching unit 11, and the apparatus control unit 12 is configured by a central processing unit (CPU) and a control program that causes the CPU to perform various processes. However, the processor 16 may be configured using a digital circuit. Further, the image generation unit 5, the display control unit 6, the measurement unit 9, the determination unit 10, the display switching unit 11, and the apparatus control unit 12 may be partially or wholly integrated into one CPU.

Figure 5:
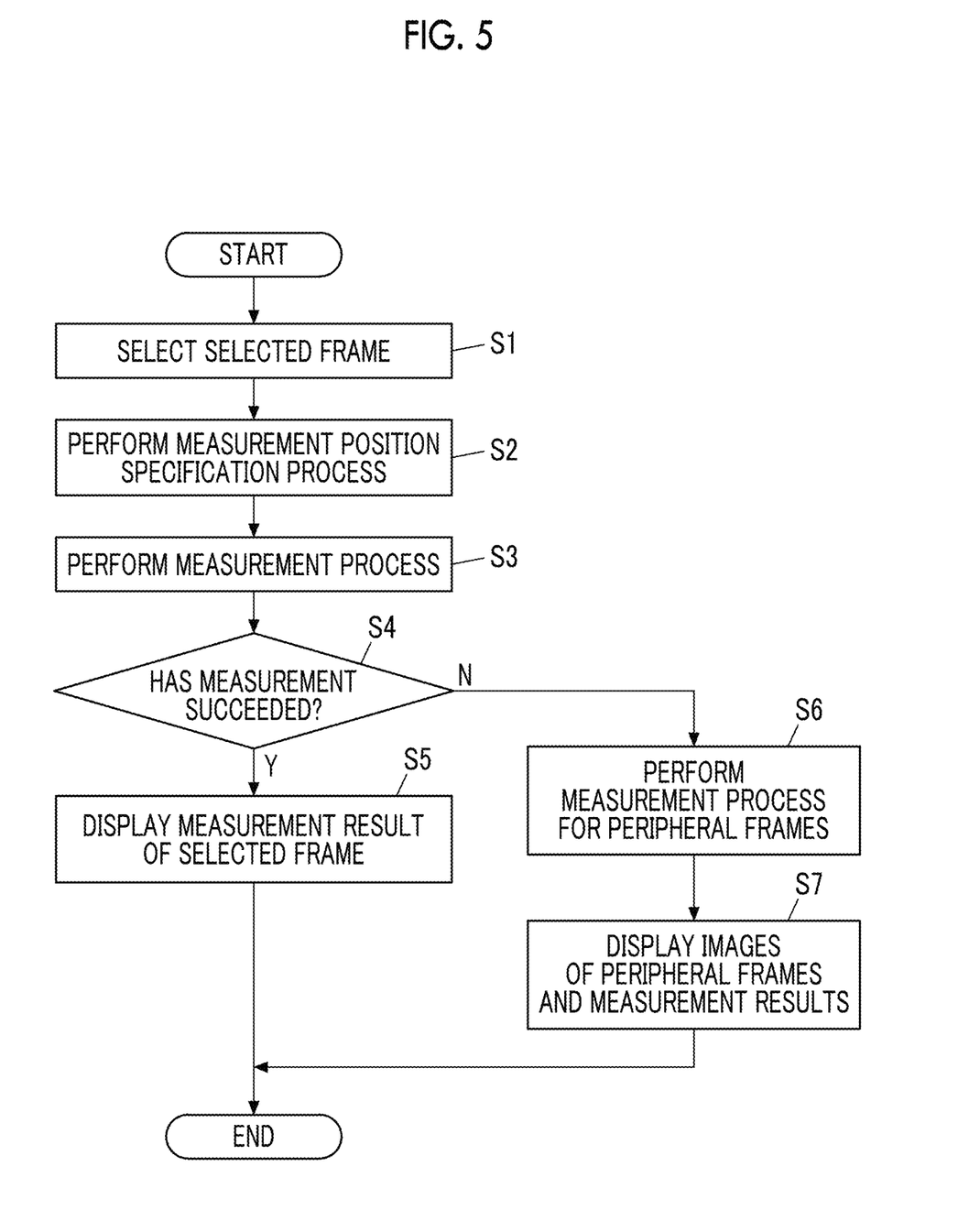
FIG. 5 is a flowchart illustrating an operation of the ultrasound diagnostic apparatus according to Embodiment 1 of the invention.

Next, the operation of the ultrasound diagnostic apparatus 1 according to Embodiment 1 will be described in detail with reference to a flowchart illustrated in FIG. 5.

Figure 6:
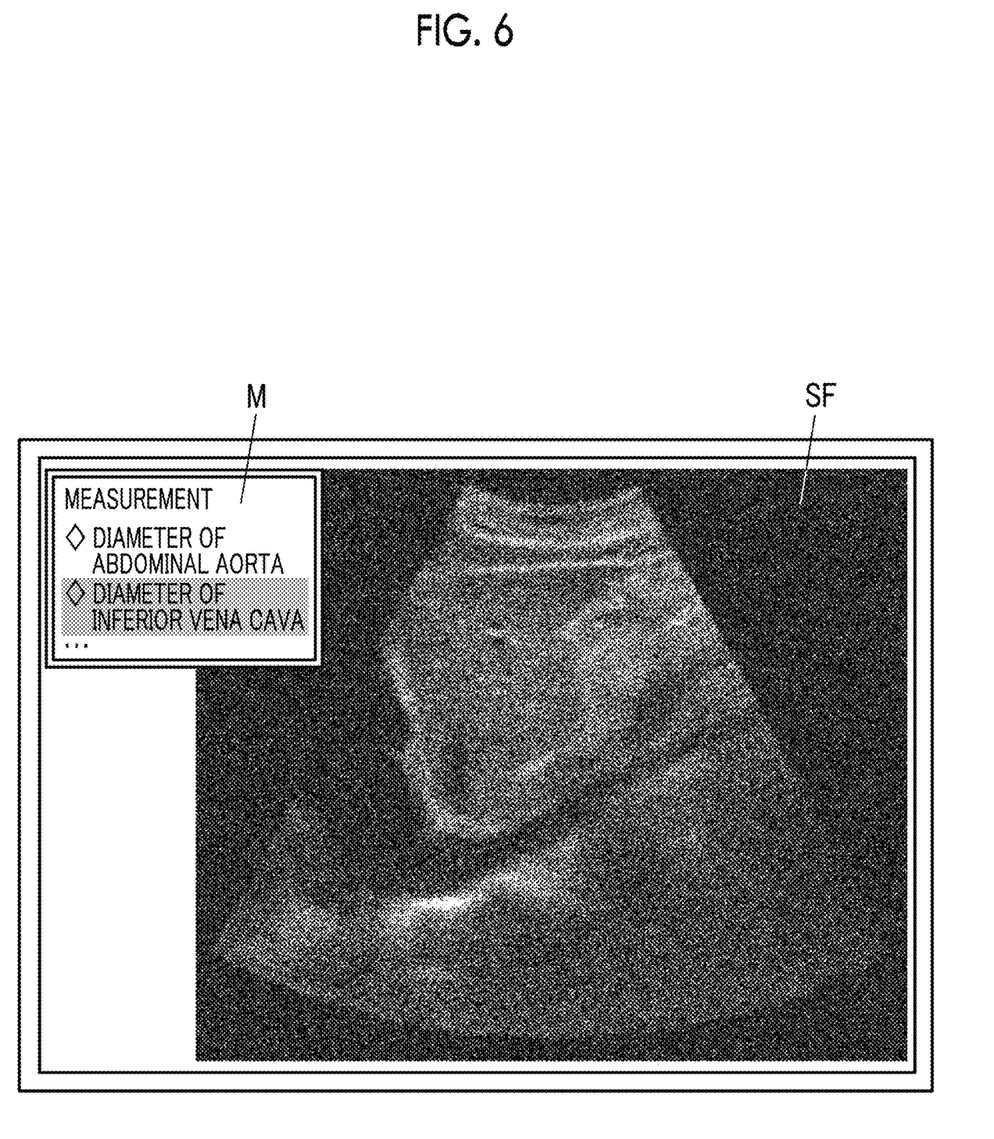
FIG. 6 is a diagram illustrating an example of the display of a list of measurement target parts in a case in which a user inputs a measurement target part in Embodiment 1 of the invention.

First, in Step S1, in a case in which the user selects one frame acquired at a time T among a plurality of frames stored in the image memory 8 through the operation unit 13, the apparatus control unit 12 receives the frame as a selected frame. In this case, the user selects a measurement target through the operation unit 13. For example, as illustrated in FIG. 6, a display of a list M indicating a plurality of measurement target candidates may be displayed on the display unit 7 so as to be superimposed on an ultrasound image of a selected frame SF and the user may select one of the plurality of measurement target candidates displayed in the display of the list M through the operation unit 13. In the example illustrated in FIG. 6, the diameter of the inferior vena cava is selected as the measurement target by the user. The display of the list M may be so-called scroll display that allows the user to perform a scroll operation to sequentially display the plurality of measurement target candidates through the operation unit 13.

Then, in Step S2, the measurement unit 9 specifies a measurement position on the ultrasound image of the selected frame SF. For example, in a case in which the diameter of the inferior vena cava is selected as the measurement target by the user, the measurement unit 9 specifies, as the measurement position MP, a position that is 2 cm to 3 cm away from the boundary B of the right atrium RA along the central axis E of the inferior vena cava C as illustrated in FIG. 4.

Figure 7:
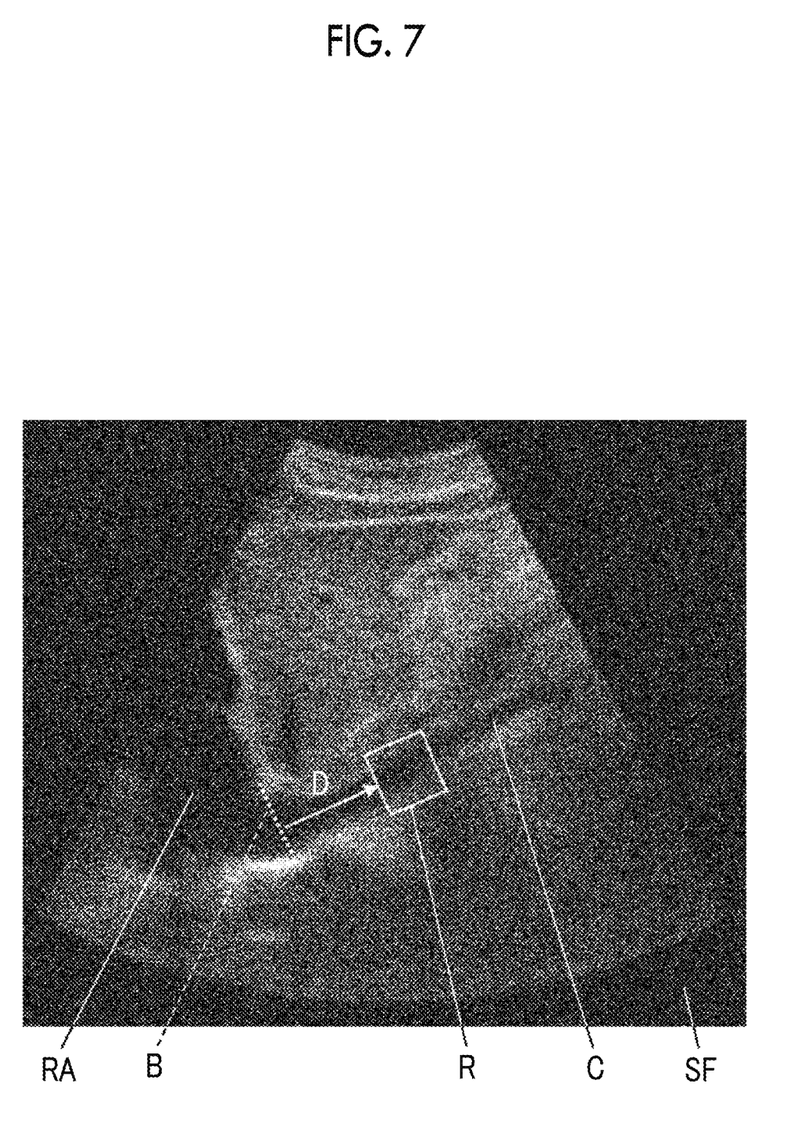
FIG. 7 is a diagram illustrating an example of the disposition of a measurement region in an ultrasound image of a selected frame in Embodiment 1 of the invention.

In this case, first, the measurement unit 9 analyzes the ultrasound image of the selected frame SF to detect the boundary B of the right atrium RA as illustrated in FIG. 7. In a case in which the boundary B of the right atrium RA is detected, the measurement unit 9 recognizes the inferior vena cava C and specifies a running direction D of the inferior vena cava C. In a case in which the running direction D of the inferior vena cava is specified, the measurement unit 9 sets a specific region R for specifying the measurement position on the ultrasound image of the selected frame SF. Here, the specific region R is a region having a width of 1 cm along the running direction D of the inferior vena cava C. The measurement unit 9 sets the specific region R such that the distance from the boundary B of the right atrium RA to the specific region R along the running direction D is 2 cm. This setting of the specific region R makes it possible to specify the measurement position MP that is 2 cm to 3 cm away from the boundary B of the right atrium RA along the central axis E of the inferior vena cava C as illustrated in FIG. 4.

Figure 8:
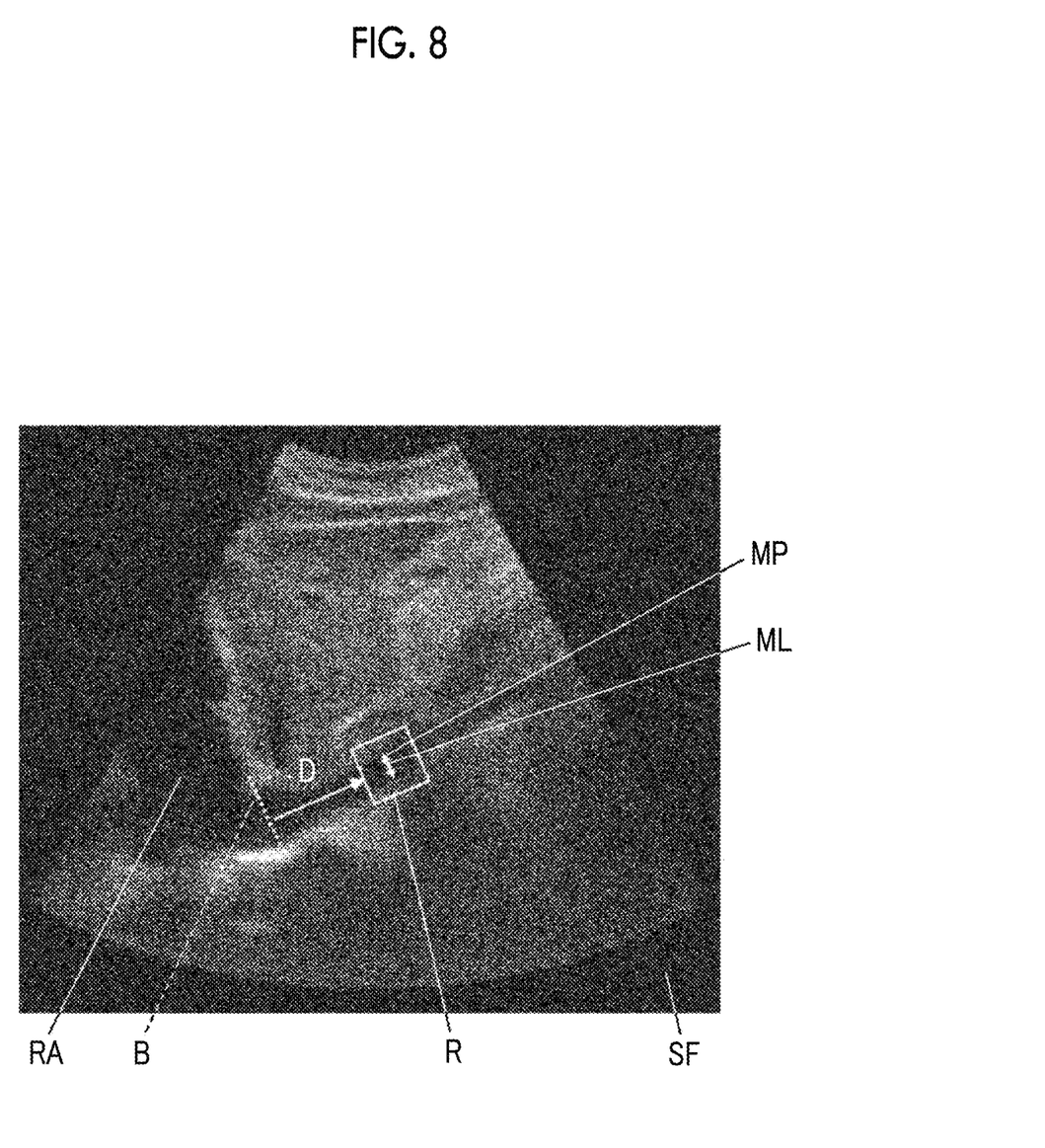
FIG. 8 is a diagram illustrating an example of the disposition of a measurement line on the ultrasound image of the selected frame in Embodiment 1 of the invention.

In a case in which the specific region R is set, the measurement unit 9 analyzes the ultrasound image in the specific region R to specify the measurement position MP illustrated in FIG. 8. For example, the measurement unit 9 can calculate the edge strength of the ultrasound image in the specific region R and specify the measurement position MP on the basis of the calculated edge strength. Here, the edge strength of the ultrasound image indicates the contour likelihood of the ultrasound image and is calculated by image analysis using, for example, the contrast between a target point and surrounding points. In this case, for example, the measurement unit 9 can determine a position where the edge strength is equal to or greater than a predetermined threshold value as the contour of the inferior vena cava in the specific region R and can specify, as the measurement position MP, the position of a line segment passing through a point where the edge strength is maximum among line segments that are perpendicular to the running direction D and have the contour of the inferior vena cava as two end points.

Then, in Step S3, the measurement unit 9 measures the measurement target on the basis of the measurement position specified in Step S2. For example, in a case in which the diameter of the inferior vena cava is selected as the measurement target by the user, the measurement unit 9 disposes a measurement line ML at the specified measurement position MP as illustrated FIG. 8 and measures the length of the measurement line ML to measure the diameter of the inferior vena cava.

Then, in Step S4, the determination unit 10 determines whether the measurement by the measurement unit 9 has succeeded or failed. Specifically, the determination unit 10 determines that the measurement by the measurement unit 9 has succeeded in a case in which a measured value is obtained in Step S3 and determines that the measurement by the measurement unit 9 has failed, for example, in a case in which the part required to specify the measurement position is not capable of being detected in Step S2 or in a case in which the part required to specify the measurement position is detected, but the measurement position is not capable of being specified. For example, in a case in which the diameter of the inferior vena cava is selected as the measurement target by the user and the boundary B of the right atrium RA required to specify the measurement position MP is not capable of being specified because the ultrasound image has an unclear part, the determination unit 10 determines that the measurement by the measurement unit 9 has failed. In addition, the determination unit 10 determines that the measurement by the measurement unit 9 has failed, for example, in a case in which the boundary B of the right atrium RA is capable of being specified and the value of the edge likelihood of the ultrasound image in the specific region R is less than a predetermined threshold value because the image of the inferior vena cava C is unclear, which makes it difficult to specify the measurement position MP.

Figure 9:
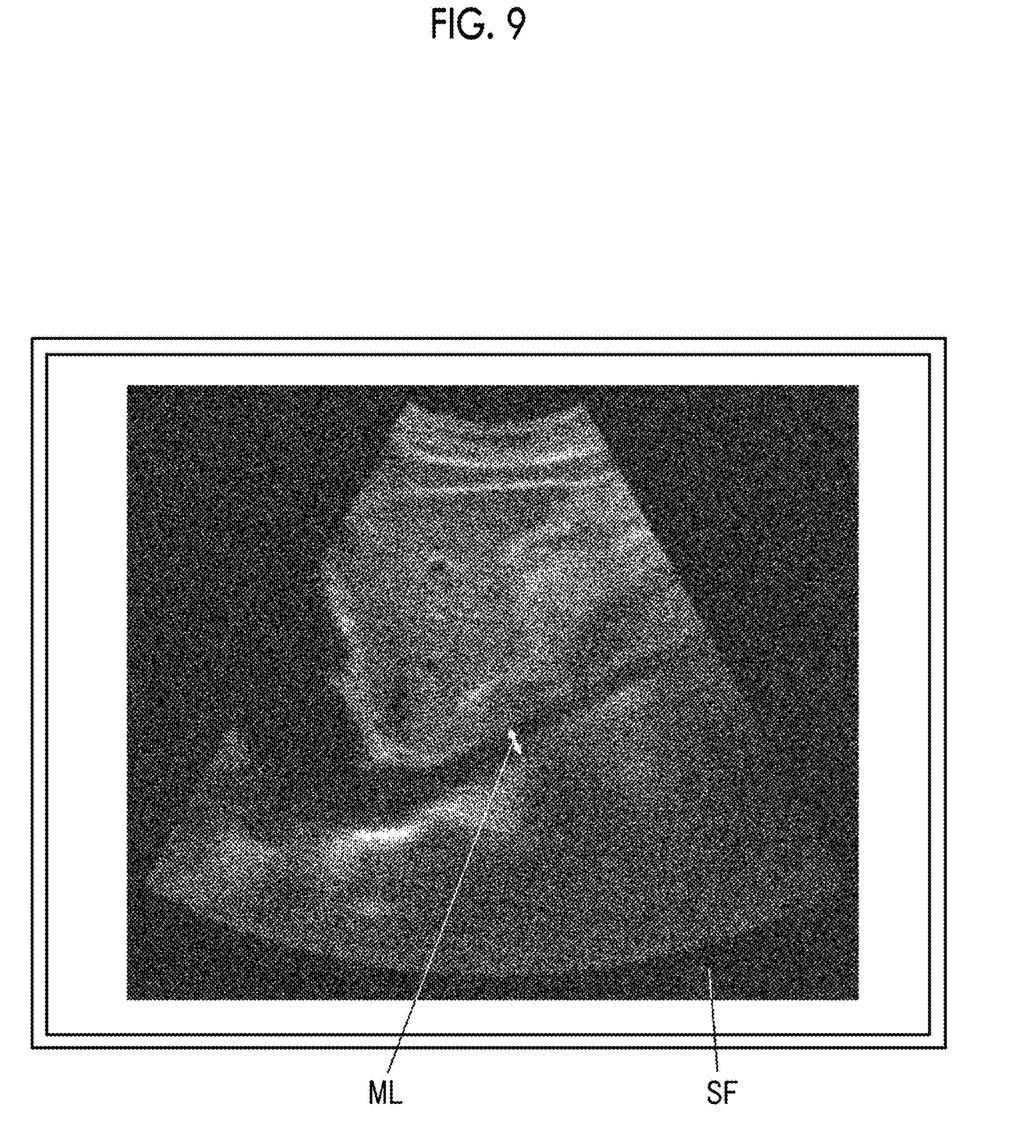
FIG. 9 is a diagram illustrating an example of the display of a measurement result for the selected frame and the ultrasound image of the selected frame in Embodiment 1 of the invention.

In Step S4, in a case in which the determination unit 10 determines that the measurement by the measurement unit 9 has succeeded, the process proceeds to Step S5. In Step S5, the display switching unit 11 displays the measurement result in the selected frame SF and the ultrasound image of the selected frame SF on the display unit 7. In this case, for example, the display switching unit 11 can display the measurement line ML as the measurement result in the selected frame SF on the display unit 7 so as to be superimposed on the ultrasound image of the selected frame SF, as illustrated in FIG. 9. Then, the operation of the ultrasound diagnostic apparatus 1 according to Embodiment 1 ends.

In a case in which the determination unit 10 determines that the measurement by the measurement unit 9 has failed in Step S4, the process proceeds to Step S6. In Step S6, the display switching unit 11 sets at least one frame different from the selected frame SF among the plurality of frames stored in the image memory 8 as a peripheral frame and directs the measurement unit 9 to perform a measure process for the at least one peripheral frame. For example, the display switching unit 11 sets a plurality of frames acquired before and after the selected frame SF in time series as the peripheral frames. Further, the measurement unit 9 performs the measurement process by performing the same process as that in Steps S2 and S3 for at least one peripheral frame.

In a case in which the measurement is performed for the peripheral frame in Step S6, in Step S7, the display switching unit 11 displays the ultrasound image of the selected frame SF, the ultrasound images of a predetermined number of peripheral frames, and the measurement results for the peripheral frames on the display unit 7. For example, as illustrated in FIG. 10, the display switching unit 11 can display four peripheral frames A1, A2, A3, and A4 as a predetermined number of peripheral images that are continuous with the selected frame SF in time series side by side with the ultrasound image of the selected frame SF.

Figure 10:
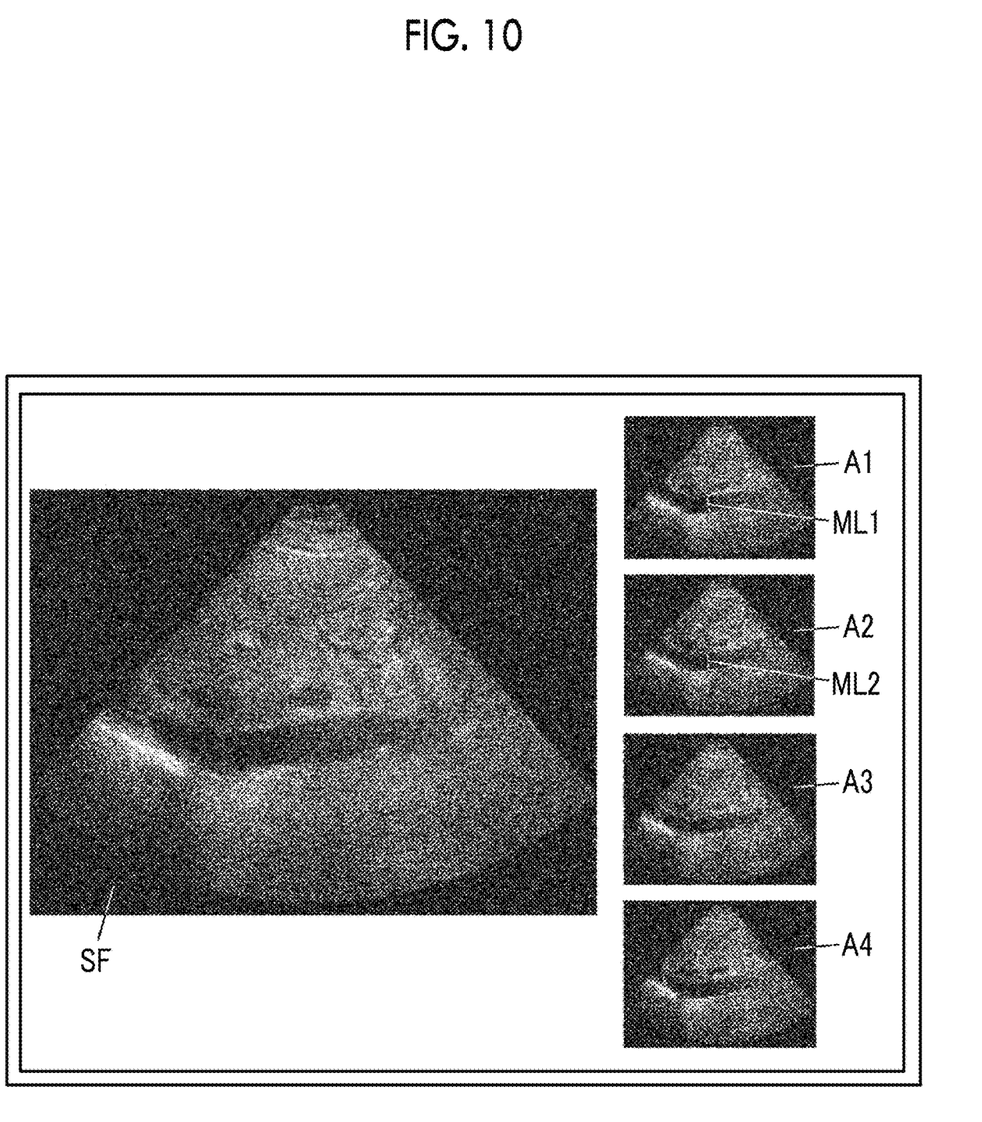
FIG. 10 is a diagram illustrating an example in which ultrasound images of peripheral frames and measurement results for the peripheral frames are displayed together with the ultrasound image of the selected frame in Embodiment 1 of the invention.

In the example illustrated in FIG. 10, the peripheral frames A1 and A2 are frames acquired before the time T when the selected frame SF was acquired and the peripheral frames A3 and A4 are frames acquired after the time T. Since the measured values are obtained for the peripheral frames A1 and A2 by the measurement unit 9, a measurement line ML1 is displayed as the measurement result of the measurement unit 9 so as to be superimposed on the peripheral frame A1 and a measurement line ML2 is displayed as the measurement result so as to be superimposed on the peripheral frame A2. In contrast, since the measured values are not obtained for the peripheral frames A3 and A4 by the measurement unit 9, measurement lines in the peripheral frames A3 and A4 are not displayed on the display unit 7. That is, in the peripheral frames A1, A2, A3, and A4, for the frame for which measurement has failed, the measurement result is not displayed on the display unit 7 and only the ultrasound image is displayed.

The user sees the display illustrated in FIG. 10 to check the positional relationship of the measurement line ML1 with respect to the ultrasound image of the peripheral frame A1 and the positional relationship of the measurement line ML2 with respect to the ultrasound image of the peripheral frame A2.

Here, the user can perform measurement for the measurement target in the ultrasound image of the selected frame SF for which measurement by the measurement unit 9 has failed with a manual operation through the operation unit 13. In this case, the user performs measurement for the selected frame SF while referring to the ultrasound image of the peripheral frame for which measurement has succeeded and the measurement result in the peripheral frame. Therefore, it is possible to perform measurement for the selected frame SF on the basis of an appropriate standard. Then, the operation of the ultrasound diagnostic apparatus 1 according to Embodiment 1 ends.

As described above, according to the ultrasound diagnostic apparatus 1 of Embodiment 1 of the invention, in a case in which the determination unit 10 determines that the measurement by the measurement unit 9 has succeeded, measurement is performed for a part of the subject on the basis of an appropriate standard. In a case in which the determination unit 10 determines that the measurement by the measurement unit 9 has failed, the ultrasound image of the selected frame SF, the measurement results in the peripheral frames, and the ultrasound images of the peripheral frames are displayed on the display unit 7 at once. Therefore, the user can perform measurement for the selected frame SF on the basis of an appropriate standard while referring to the measurement results in the ultrasound images of the peripheral frames. As described above, according to the ultrasound diagnostic apparatus 1, even in a case in which the determination unit 10 determines that the measurement by the measurement unit 9 has failed, it is possible to perform measurement for a part of the subject on the basis of an appropriate standard, regardless of the skill level of the user.

In Embodiment 1, the transmitting unit 3 and the receiving unit 4 are included in the ultrasound probe 15, but may be included in the processor 16.

In Embodiment 1, the measurement unit 9 performs measurement for a plurality of frames which have been generated by the image generation unit 5 and then stored in the image memory 8. However, the image memory 8 may be connected to an external device, such as a server, and may store the ultrasound images of a plurality of frames input from the outside.

Further, in Embodiment 1, in a case in which the determination unit 10 determines that measurement for the selected frame SF has failed, the display switching unit 11 displays the frame acquired before the selected frame SF and the frame acquired after the selected frame SF in time series on the display unit 7. However, the display switching unit 11 may display any one of the frame acquired before the selected frame SF or the frame acquired after the selected frame SF in time series on the display unit 7. In this case, the user can also perform measurement for the measurement target in the selected frame SF on the basis of an appropriate standard with a manual operation through the operation unit 13 while referring to the measurement results in the ultrasound images of the peripheral frames.

In Embodiment 1, in a case in which the determination unit 10 determines that measurement for the selected frame SF has failed, the ultrasound images of the plurality of peripheral frames A1, A2, A3, and A4 and the measurement results in the peripheral frames A1 and A2 are displayed on the display unit 7. However, the display switching unit 11 may display an ultrasound image of one peripheral frame and the measurement result in the peripheral frame on the display unit 7. In this case, the user can also check the ultrasound image of the selected frame SF, an ultrasound image of one peripheral frame, and the measurement result in the peripheral frame at one time. Therefore, in a case in which measurement for the selected frame SF is performed by a manual operation, it is possible to perform the measurement on the basis of an appropriate standard. In the peripheral frames, the measurement result for the frame for which measurement has failed is not displayed on the display unit 7 and only the ultrasound image of the peripheral frame is displayed.

In a case in which the determination unit 10 determines that measurement for the selected frame SF has failed, the display switching unit 11 sets, as the peripheral frames, all of the frames that are continuous in time series with the selected frame SF among the plurality of frames stored in the image memory 8, directs the measurement unit 9 to perform a measurement process for the peripheral frames, and displays the ultrasound images of the peripheral frames and the measurement results in the peripheral frames on the display unit 7. In this case, in the peripheral frames, the measurement result for the frame for which measurement has failed is not displayed on the display unit 7 and only the ultrasound image of the peripheral frame is displayed.

In Embodiment 1, in a case in which the determination unit 10 determines that measurement for the selected frame SF has failed, a plurality of peripheral frames and the measurement results in the peripheral frames are displayed on the display unit 7 at once. However, the display switching unit 11 may display a plurality of peripheral frames and the measurement results in the peripheral frames in a so-called scroll display manner. In this case, the user can perform measurement for the selected frame SF with a manual operation while referring to the peripheral frames and the measurement results in the peripheral frames. That is, the display of the ultrasound image of the peripheral frame and the measurement result in the peripheral frame includes scroll display.

There are some parts of the subject that move periodically, such as the inferior vena cava and the aorta. For example, the diameter of the inferior vena cava is changed by a change in the internal pressure of the right atrium due to the breathing of the subject. In this case, the diameter of the inferior vena cava is reduced by the deep breath of air by the subject. Therefore, the diameter of the inferior vena cava is periodically changed by the periodic deep breath of air by the subject. Further, for example, the diameter of the aorta changes periodically due to the heartbeat. In a case in which measurement is performed for the part, it is possible to use frames within one cycle following the movement of the part. In a case in which the determination unit 10 determines that measurement for the selected frame SF has failed, the display switching unit 11 can set all frames other than the selected frame SF among a plurality of frames in one cycle as the peripheral frames and can display the ultrasound images of the peripheral frames and the measurement results in the peripheral frames on the display unit 7. Therefore, in a case in which the image memory 8 stores the frames acquired in a plurality of cycles, it is possible to prevent a measurement process from being performed for frames equal to or greater than the necessary number of frames and to prevent frames whose number is equal to or greater than necessary as the peripheral frames from being displayed on the display unit 7. In addition, it is possible to reduce the calculation load of the ultrasound diagnostic apparatus 1.

Further, in Embodiment 1, in a case in which the determination unit 10 determines that measurement for the selected frame SF has failed, the measurement unit 9 performs the measurement process for a plurality of peripheral frames. However, the determination unit 10 may determine whether measurement for a plurality of peripheral frames subjected to the measurement process has succeeded or failed. In this case, the display switching unit 11 may display, on the display unit 7, only some frames from a frame subsequent to the selected frame SF to a frame, for which the determination unit 10 determines that measurement has succeeded first, after the selected frame SF in time series or only some frames from a frame, for which the determination unit 10 determines that measurement has succeeded first, before the selected frame SF to a frame immediately before the selected frame SF in time series among a plurality of peripheral frames. Therefore, the user can see the display unit 7 to check the peripheral frame for which measurement has succeeded and the measurement result in the peripheral frame while checking the state of the measurement target part that continuously changes for the selected frame SF.

In a case in which the determination unit 10 determines that measurement for the selected frame SF has failed and determines whether measurement for a plurality of peripheral frames subjected to the measurement process has succeeded or failed, the display switching unit 11 can display, on the display unit 7, only the frame, for which the determination unit 10 determines that the measurement has succeeded, among the plurality of peripheral frames. Therefore, the user can perform measurement for the selected frame SF with a manual operation on the basis of an appropriate standard while easily checking the peripheral frame for which measurement has succeeded.

Embodiment 2

The display switching unit 11 may notify the user that an error has occurred in a case in which the determination unit 10 determines that measurement for the selected frame SF has failed and measurement for all of the peripheral frames has failed. Here, an ultrasound diagnostic apparatus 1 according to Embodiment 2 has the same configuration as the ultrasound diagnostic apparatus 1 according to Embodiment 1 illustrated in FIG. 1.

Figure 11:
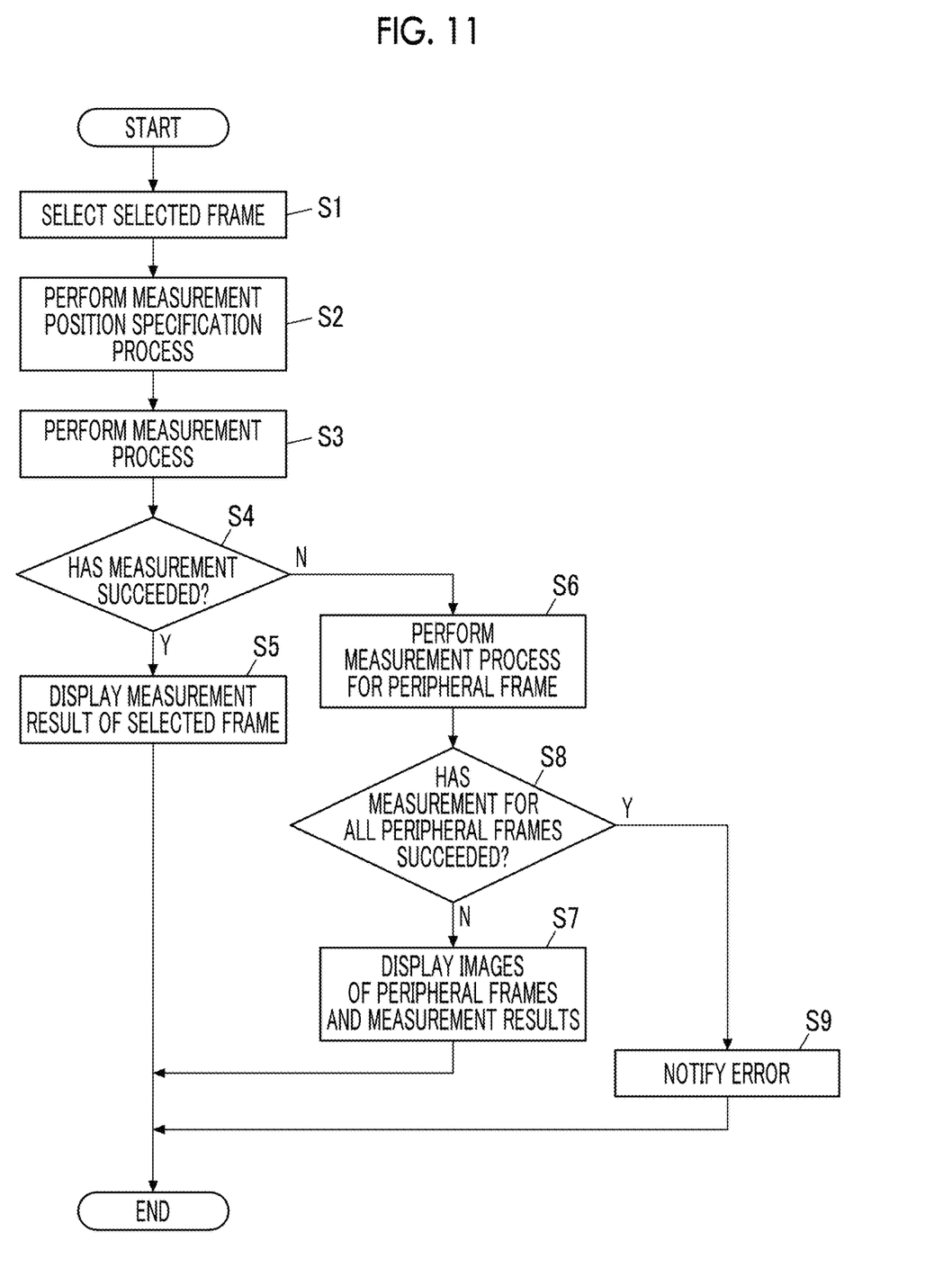
FIG. 11 is a flowchart illustrating an operation of an ultrasound diagnostic apparatus according to Embodiment 2 of the invention.

FIG. 11 is a flowchart illustrating the operation of the ultrasound diagnostic apparatus 1 according to Embodiment 2. Steps S1 to S7 in this flowchart are the same as Steps S1 to S7 in the flowchart illustrated in FIG. 5, respectively.

First, in Step S1, the user selects one of a plurality of frames stored in the image memory 8 as the selected frame SF through the operation unit 13. In this case, a measurement target, such as the diameter of the inferior vena cava, is selected by the user through the operation unit 13.

Then, in Step S2, the measurement unit 9 analyzes the ultrasound image of the selected frame SF to specify a measurement position corresponding to the measurement target selected by the user in Step S1. In a case in which the measurement position is specified, the process proceeds to Step S3 and the measurement unit 9 performs a measurement process for the measurement target on the basis of the specified measurement position.

Then, in Step S4, the determination unit 10 determines whether the measurement by the measurement unit 9 has succeeded or failed. In a case in which the determination unit 10 determines that the measurement by the measurement unit 9 has succeeded, the process proceeds to Step S5 and the ultrasound image of the selected frame SF and the measurement result in the selected frame SF are displayed on the display unit 7.

In a case in which the determination unit 10 determines that the measurement by the measurement unit 9 has failed in Step S4, the process proceeds to Step S6. In Step S6, the display switching unit 11 sets at least one frame different from the selected frame SF among the plurality of frames stored in the image memory 8 as a peripheral frame and the measurement unit 9 performs the measurement process for the at least one peripheral frame.

Then, in Step S8, the determination unit 10 determines whether or not measurement for all of the peripheral frames has failed. Here, in a case in which there is a peripheral frame for which the measurement by the measurement unit 9 has succeeded, the process proceeds to Step S7. In Step S7, the display switching unit 11 displays the ultrasound image of the selected frame SF, the ultrasound image of the peripheral frame, and the measurement result in the peripheral frame on the display unit 7.

In Step S8, in a case in which the determination unit 10 determines that measurement for all of the peripheral frames has failed, the process proceeds to Step S9. In Step S9, the display switching unit 11 displays an error indication indicating that an error has occurred on the display unit 7, which is not illustrated.

Thus, the operation of the ultrasound diagnostic apparatus 1 according to Embodiment 2 ends.

As described above, according to the ultrasound diagnostic apparatus 1 of Embodiment 2, in a case in which measurement for all of the peripheral frames has failed, an error indication indicating that an error has occurred is displayed on the display unit 7. Therefore, for example, in a case in which a plurality of frames that are continuous with the selected frame SF in time series are used, it is possible to make the user aware of that it may be difficult to perform measurement on the basis of an appropriate standard defined in, for example, the guideline and to call the attention of the user to measurement.

EXPLANATION OF REFERENCES

1: ultrasound diagnostic apparatus
2: transducer array
3: transmitting unit
4: receiving unit
5: image generation unit
6: display control unit
7: display unit
8: image memory
9: measurement unit
10: determination unit
11: display switching unit
12: apparatus control unit
13: operation unit
14: storage unit
15: ultrasound probe
16: processor
17: amplification unit
18: AD conversion unit
19: signal processing unit
20: DSC
21: image processing unit
A1, A2, A3, A4: peripheral frame
B: boundary
C: inferior vena cava
D: running direction
E: central axis
L: distance
M: display of list
ML, ML1, ML2: measurement line
MP: measurement position
R: specific region
RA: right atrium
SF: selected frame

What is claimed is:
1. An ultrasound diagnostic apparatus comprising:
an imaging device configured to perform imaging to capture ultrasound images of a plurality of frames which are continuous in time series and include a measurement target part of a subject as a measurement target;
an image memory configured to store the ultrasound images;
a monitor configured to display an ultrasound image of a selected frame which is one of the plurality of frames selected by a user; and
a processor configured to
perform specifying measurement positions on the ultrasound image of the selected frame by analyzing the ultrasound image of the selected frame,
perform measurement for the measurement target part of the subject based on the measurement positions on the ultrasound image of the selected frame, in a case where a measurement target result is obtained for the measurement target part of the subject, determine that the measurement for the measurement target has succeeded, and display a measurement result in the selected frame on the monitor, in a case where the measurement positions on the ultrasound image of the selected frame are not capable of being specified, determine that the measurement for the measurement target has failed, perform specifying measurement positions on an ultrasound image of at least one peripheral frame different from the selected frame among the plurality of frames stored in the image memory by analyzing the ultrasound image of the at least one peripheral frame, perform measurement for the measurement target part of the subject based on the measurement positions on the ultrasound image of the at least one peripheral frame, and display the ultrasound image of the at least one peripheral frame and a measurement result in the at least one peripheral frame on the monitor, wherein the processor is configured to automatically determine whether the measurement for the measurement target has succeeded or failed based on the ultrasound image of the selected frame.

2. The ultrasound diagnostic apparatus according to claim 1, wherein, in a case in which the measurement for the selected frame has been determined to be failed, the processor is further configured to display a frame, for which the measurement has been determined to be succeeded, among the at least one peripheral frame so as to be highlighted.

3. The ultrasound diagnostic apparatus according to claim 1, wherein the at least one peripheral frame is a frame, for which the measurement has been determined to be succeeded, in a case in which the measurement for the selected frame has been determined to be failed.

4. The ultrasound diagnostic apparatus according to claim 1, wherein, in a case in which the measurement target part is an inferior vena cava, the processor is further configured to detect a boundary of a right atrium of the subject, specify a measurement position determined from the detected boundary of the right atrium, measure a diameter of the inferior vena cava at the specified measurement position, and determine that the measurement has failed in a case in which the boundary of the right atrium is not detected or in a case in which the measurement position is not specified.

5. The ultrasound diagnostic apparatus according to claim 1, wherein the measurement result includes a measurement line for performing measurement for the measurement target part of the subject.

6. The ultrasound diagnostic apparatus according to claim 1, wherein the at least one peripheral frame is a predetermined number of frames continuous with the selected frame.

7. The ultrasound diagnostic apparatus according to claim 6, wherein, in a case in which the measurement for the selected frame has been determined to be failed, the processor is further configured to display a frame, for which the measurement has been determined to be succeeded, among the at least one peripheral frame so as to be highlighted.

8. The ultrasound diagnostic apparatus according to claim 1, wherein the at least one peripheral frame is all frames other than the selected frame in a series of frames under measurement.

9. The ultrasound diagnostic apparatus according to claim 8, wherein, in a case in which the measurement for the selected frame has been determined to be failed, the processor is further configured to display a frame, for which the measurement has been determined to be succeeded, among the at least one peripheral frame so as to be highlighted.

10. The ultrasound diagnostic apparatus according to claim 1, wherein the plurality of frame includes a first part consist of frames after the selected frame and a second part consist of frames before the selected frame, in a case where the measurement for the selected frame has been determined to be failed and the measurements for some frames in the first part have been determined to be succeeded, the processor is further configured to display frames from a frame subsequent to the selected frame to a frame for which the measurement has succeeded at first among the first part, on the monitor, in a case where the measurement for the selected frame has been determined to be failed and the measurements for some frames in the second part have been determined to be succeeded, the processor is further configured to display frames from a frame for which the measurement has succeeded at last among the second part to a frame immediately before the selected frame, on the monitor.

11. The ultrasound diagnostic apparatus according to claim 10, wherein, in a case in which the measurement for the selected frame has been determined to be failed, the processor is further configured to display a frame, for which the measurement has been determined to be succeeded, among the at least one peripheral frame so as to be highlighted.

12. The ultrasound diagnostic apparatus according to claim 1, wherein, in a case in which the measurement target part is a part which moves periodically, the at least one peripheral frame is all frames other than the selected frame among frames in one cycle which include the selected frame and follow the periodic movement of the measurement target part.

13. The ultrasound diagnostic apparatus according to claim 12, wherein the measurement target part is a part that moves periodically due to breathing of the subject.

14. The ultrasound diagnostic apparatus according to claim 12, wherein the measurement target part is a part that moves periodically due to a heartbeat of the subject.

15. The ultrasound diagnostic apparatus according to claim 12, wherein, in a case in which the measurement for the selected frame has been determined to be failed, the processor is further configured to display a frame, for which the measurement has been determined to be succeeded, among the at least one peripheral frame so as to be highlighted.

\* \* \* \* \*